(12) United States Patent
Fuller et al.

(10) Patent No.: US 10,905,844 B2
(45) Date of Patent: Feb. 2, 2021

(54) METERING VALVE FOR A METERED DOSE INHALER

(71) Applicants: DunAn Microstaq, Inc., Austin, TX (US); Pearl Therapeutics, Inc., Redwood City, CA (US)

(72) Inventors: E. Nelson Fuller, Manchester, MI (US); Parthiban Arunasalam, Austin, TX (US); Joseph Nguyen, Austin, TX (US); Joe A. Ojeda, Sr., Austin, TX (US); Wayne Curtis Long, Austin, TX (US); Michael Thomas Riebe, Bradenton, FL (US); Matthew Skelly Ferriter, Chapel Hill, NC (US); Jill Karen Sherwood, Raleigh, NC (US); Daniel Marion Deaton, III, New Hill, NC (US); Michael Leon Franklin, Cary, NC (US)

(73) Assignees: DunAn Microstaq, Inc., Austin, TX (US); Pearl Therapeutics, Inc., Redwood City, CA (US)

( * ) Notice: Subject to any disclaimer, the term of this patent is extended or adjusted under 35 U.S.C. 154(b) by 219 days.

(21) Appl. No.: 16/266,342

(22) Filed: Feb. 4, 2019

(65) Prior Publication Data
US 2019/0167939 A1    Jun. 6, 2019

Related U.S. Application Data

(62) Division of application No. 14/988,139, filed on Jan. 5, 2016, now Pat. No. 10,589,052.

(Continued)

(51) Int. Cl.
*A61M 15/00* (2006.01)
*A61M 16/20* (2006.01)
(Continued)

(52) U.S. Cl.
CPC ...... *A61M 16/201* (2014.02); *A61M 5/16813* (2013.01); *A61M 15/008* (2014.02);
(Continued)

(58) Field of Classification Search
CPC ........ A61M 11/00; A61M 11/001–008; A61M 11/02–08; A61M 13/00;
(Continued)

(56) References Cited

U.S. PATENT DOCUMENTS

| 5,404,871 A * | 4/1995 | Goodman | A61M 15/00 128/200.14 |
| 7,748,378 B2 | 7/2010 | Hodson | |
| 2014/0373937 A1 * | 12/2014 | Fuller | F16K 99/0021 137/197 |

* cited by examiner

*Primary Examiner* — Jan Christopher L Merene
*Assistant Examiner* — Ned T Heffner
(74) *Attorney, Agent, or Firm* — MacMillan, Sobanski & Todd, LLC

(57) ABSTRACT

An improved aerosol dispensing apparatus includes an aerosol container, a discharge piece movably mounted to the aerosol container, a flow control valve mounted within the discharge piece, a battery, and an electronically controlled metering valve electronically connected to the battery and in fluid communication with the flow control valve. The flow control valve is movable between an open position wherein a volume of an aerosol formulation is directed from the aerosol container through the flow control valve to the metering valve, and a closed position, wherein the metering valve is configured to precisely control a flow of the aerosol formulation outward of the discharge piece. A solenoid is electronically connected to the battery and is movable between an actuated position wherein the solenoid urges the flow control valve into the open position, and an un-actuated position wherein the flow control valve remains in the closed position.

7 Claims, 14 Drawing Sheets

Related U.S. Application Data

(60) Provisional application No. 62/222,341, filed on Sep. 23, 2015, provisional application No. 62/099,822, filed on Jan. 5, 2015.

(51) Int. Cl.
*A61M 5/168* (2006.01)
*A61M 39/24* (2006.01)
*A61M 39/22* (2006.01)

(52) U.S. Cl.
CPC ...... *A61M 15/009* (2013.01); *A61M 15/0066* (2014.02); *A61M 16/202* (2014.02); *A61M 2039/226* (2013.01); *A61M 2039/2473* (2013.01); *A61M 2205/3334* (2013.01); *A61M 2205/50* (2013.01); *A61M 2205/581* (2013.01); *A61M 2205/583* (2013.01); *A61M 2205/8206* (2013.01)

(58) Field of Classification Search
CPC .... A61M 15/00–0011; A61M 15/0028; A61M 15/0065–0078; A61M 15/0085; A61M 15/009; A61M 15/06; A61M 15/08; A61M 15/085
See application file for complete search history.

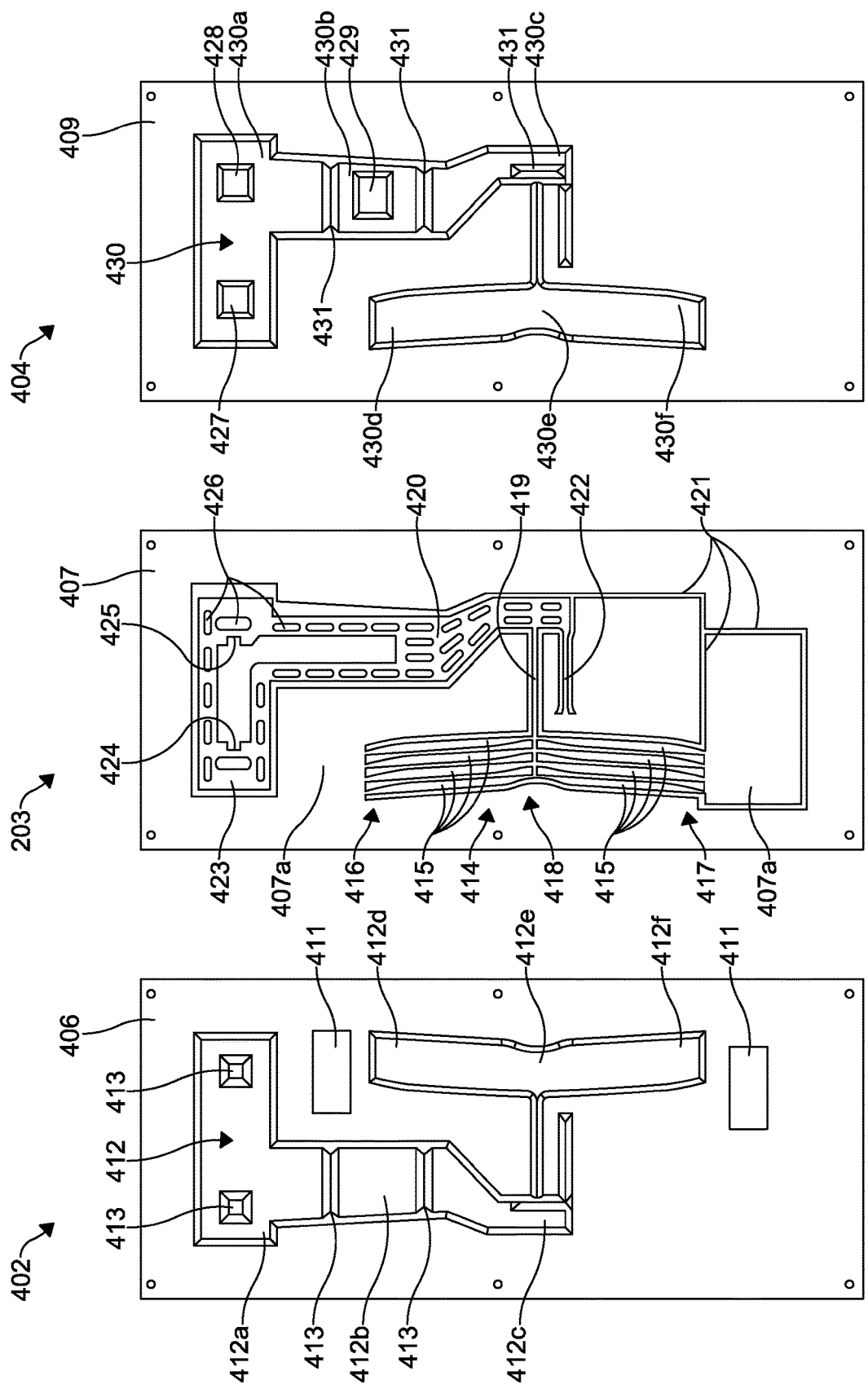

METERING VALVE FOR A METERED DOSE INHALER

BACKGROUND OF THE INVENTION

This invention relates in general to aerosol dispensing apparatus. In particular, this invention relates to an improved aerosol dispensing apparatus having either a metering valve or a flow control valve in combination with an electronically actuated microvalve and configured for use in dispensing aerosol formulations.

A conventional aerosol dispensing apparatus may have a metering valve that provides a means by which aerosols are dispensed from an attached aerosol container. Such metering valves are useful for administering medicinal formulations to a patient in aerosol form.

When administering medicinal formulations, a dose of the medicinal formulation sufficient to produce a desired physiological response is delivered to the patient. It is important that a predetermined amount of the medicinal formulation be dispensed to the patient in each successive dose. Therefore, any dispensing system must be able to dispense doses of the medicinal formulation accurately and reliably.

A metering valve may be used in an aerosol dispensing apparatus, such as a metered dose inhaler, to regulate the volume of a medicinal formulation passing from an aerosol container to a metering chamber. The metering chamber defines the maximum amount of the medicinal formulation that will be dispensed as a dose to the patient. Many aerosol dispensing apparatus rely on a controllable flow of the medicinal formulation into the metering chamber to control the accuracy and/or precision of successive metered doses of the medicinal formulation. The flow of the medicinal formulation through a conventional metering valve may become disrupted however, resulting in inconsistent or inaccurate doses of the medicinal formulation. Thus, it would be desirable to provide an improved structure for an aerosol dispensing apparatus that allows for more precise control of dosages of medicinal formulations in aerosol form.

SUMMARY OF THE INVENTION

This invention relates to an improved structure for an aerosol dispensing apparatus for use in dispensing aerosol formulations. In one embodiment, the improved aerosol dispensing apparatus includes an aerosol container, a discharge piece movably mounted to the aerosol container, a flow control valve mounted within the discharge piece, a battery, and an electronically controlled metering valve electronically connected to the battery and in fluid communication with the flow control valve. The flow control valve is movable between an open position wherein a volume of an aerosol formulation is directed from the aerosol container through the flow control valve to the metering valve, and a closed position, wherein the metering valve is configured to precisely control a flow of the aerosol formulation outward of the discharge piece. A solenoid is electronically connected to the battery and is movable between an actuated position wherein the solenoid urges the flow control valve into the open position, and an un-actuated position wherein the flow control valve remains in the closed position.

In another embodiment, the improved aerosol dispensing apparatus includes an aerosol container, a discharge piece movably mounted to the aerosol container, a flow control valve mounted within the discharge piece, a battery and an electronically controlled metering valve electronically connected to the battery and in fluid communication with the flow control valve. The flow control valve is movable between an open position wherein a volume of an aerosol formulation is directed from the aerosol container through the flow control valve to the metering valve, and a closed position wherein the aerosol formulation is not permitted to flow through the flow control valve to the metering valve, and wherein the metering valve is configured to precisely control a flow of the aerosol formulation outward of the discharge piece.

Various advantages of the invention will become apparent to those skilled in the art from the following detailed description, when read in view of the accompanying drawings.

BRIEF DESCRIPTION OF THE DRAWINGS

FIG. 16 is a top plan view of an inner surface of the cover plate illustrated in FIGS. 14 and 15.

FIG. 17 is a top plan view of the intermediate plate illustrated in FIGS. 14 and 15.

FIG. 18 is a top plan view of an inner surface of the base plate illustrated in FIGS. 14 and 15.

DETAILED DESCRIPTION OF THE INVENTION

Figure 1:
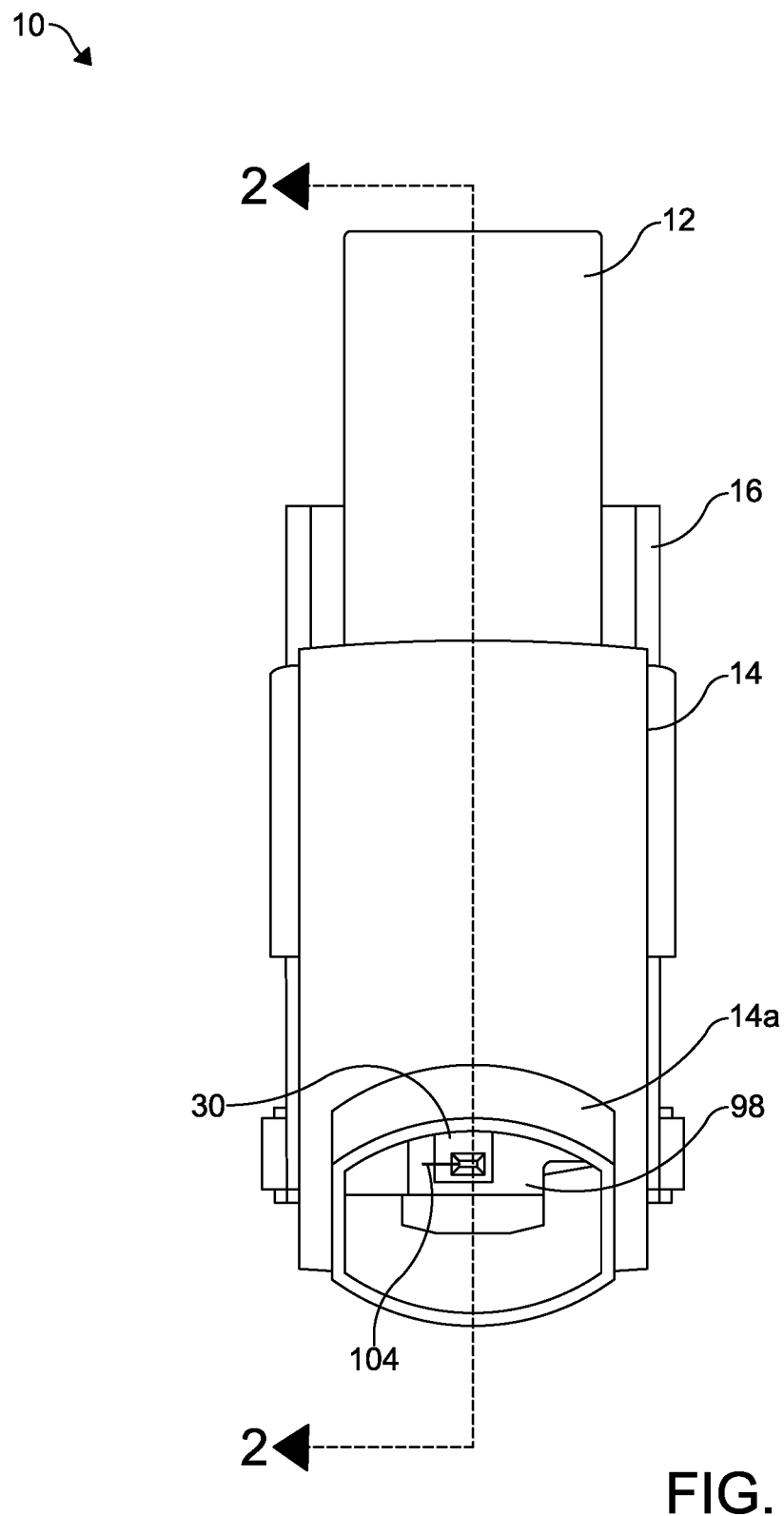
FIG. 1 an elevational view of a first embodiment of an improved aerosol dispensing apparatus according to this invention.

This invention relates to an improved structure for a metering valve for an aerosol dispensing apparatus for use in dispensing aerosol formulations. Referring now to FIGS. 1 through 4, a first embodiment of an improved aerosol dispensing apparatus is shown at 10. The aerosol dispensing apparatus 10 includes an aerosol container 12 mounted within a discharge piece 14. A battery housing 16 is attached to the discharge piece 14 and contains a battery 18.

Figure 2:
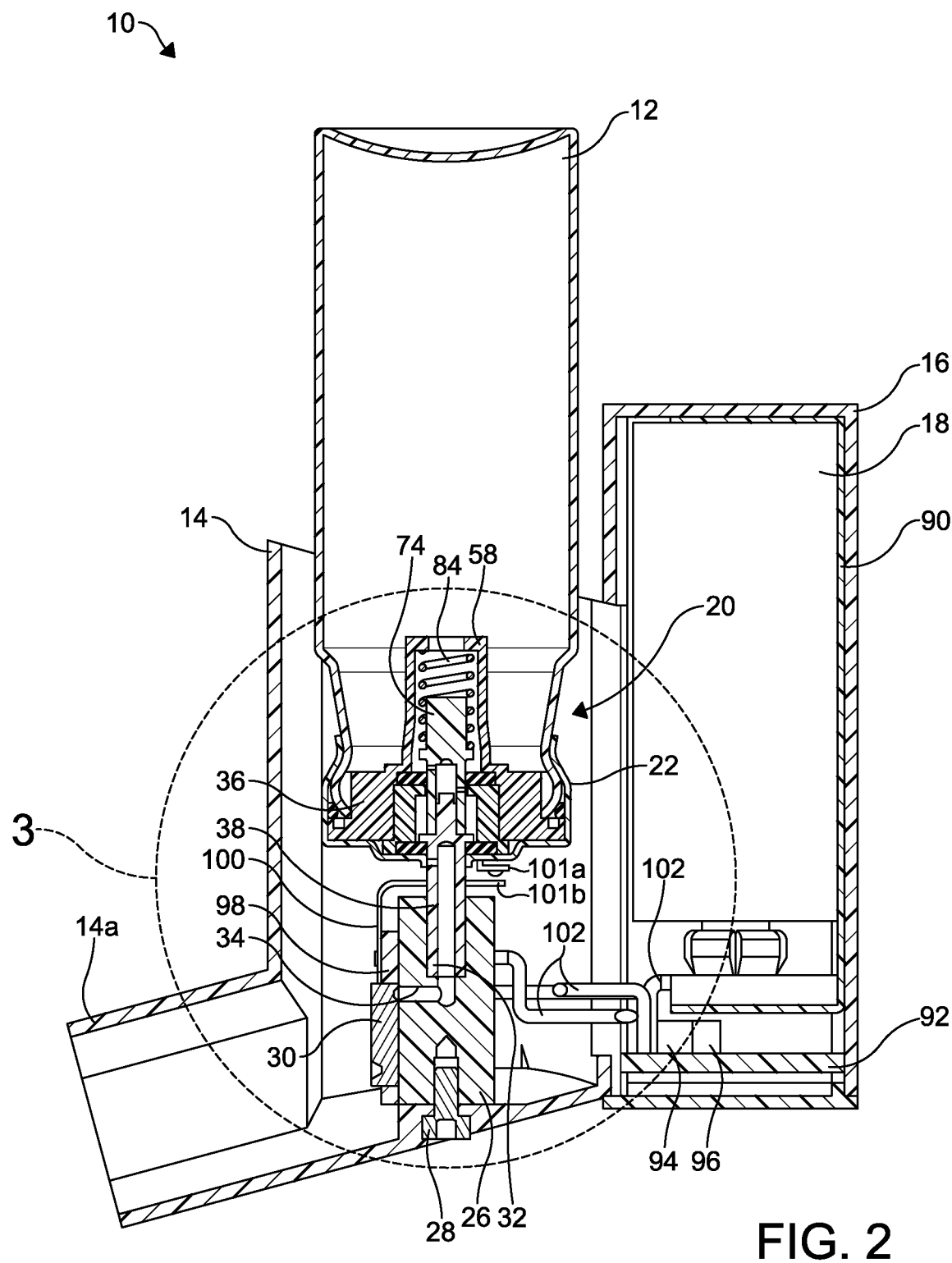
FIG. 2 is a cross-sectional elevational view of the improved aerosol dispensing apparatus taken along the line 2-2 of FIG. 1.
Figure 3:
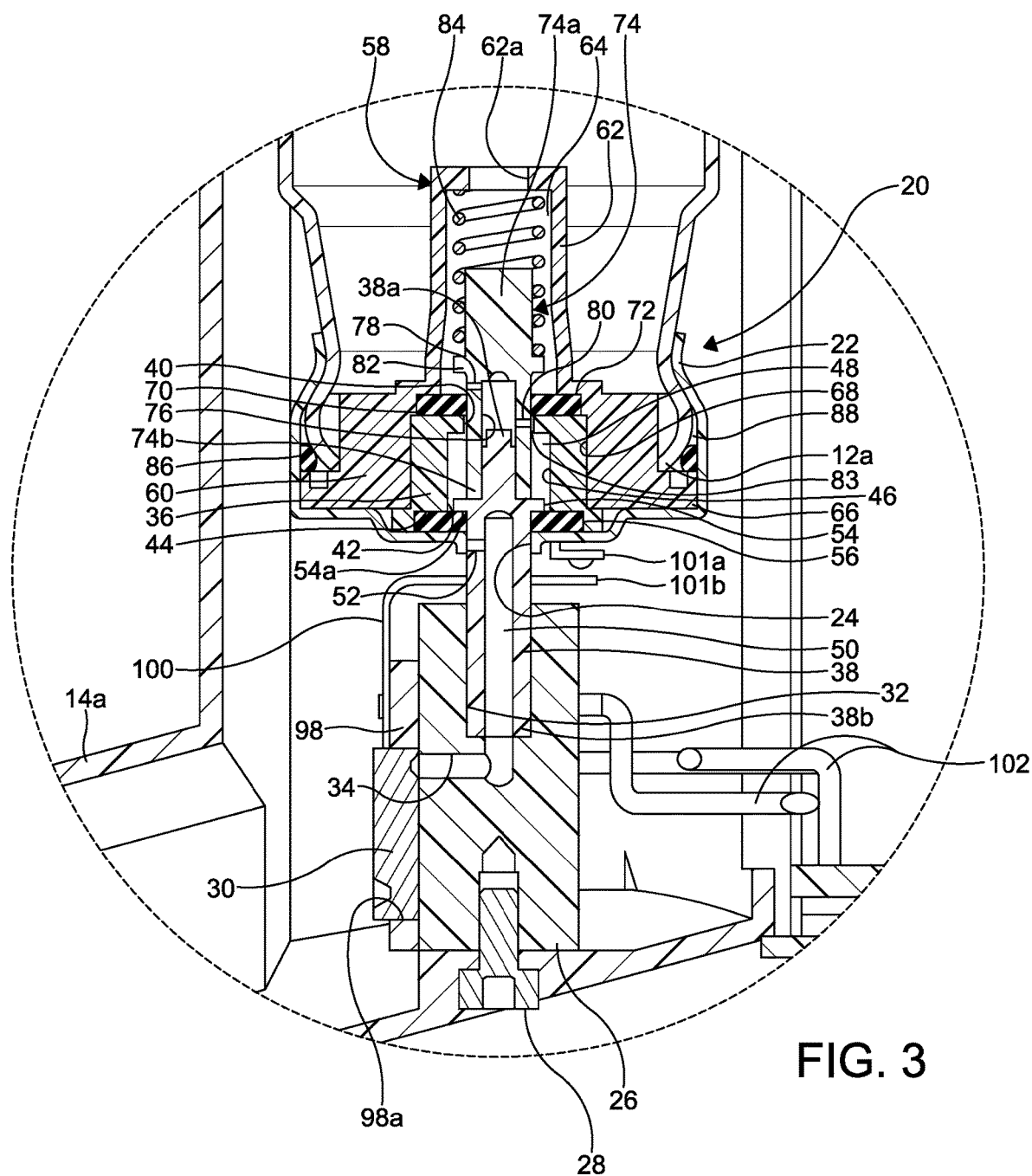
FIG. 3 is an enlarged cross-sectional view of a portion of the improved aerosol dispensing apparatus illustrated in FIG. 2.

As best shown in FIGS. 2 and 3, a metering valve is shown at 20. The metering valve 20 includes a substantially cup-shaped valve housing 22 having a centrally formed stem opening 24 formed in a bottom surface thereof. A first or open end of the valve housing 22 is attached to an open end 12a of the aerosol container 12 such as by crimping. Alternatively, the valve housing 22 may be attached to the aerosol container 12 by other means, such as with an adhesive, with a laser weld, and with an electronic beam weld.

A valve block 26 is mounted to an inside surface of the discharge piece 14 by any desired means, such as by a threaded fastener 28. The valve block 26 includes an axially extending stem bore 32 and a transverse fluid passageway 34 that is in fluid communication with the microvalve 30.

An electronically controlled flow control valve is mounted to an outside surface of the valve block 26. In the illustrated embodiment, the flow control valve is an electronically actuated microvalve 30, the structure and function of which is described below. Alternatively, the flow control valve may be any relatively small; i.e., able to fit within the discharge piece 14, electronically controlled flow control valve, such as a solenoid valve.

The metering valve 20 further includes a valve body 36 seated within the valve housing 22. The valve body 36 is substantially cylindrical in shape and defines a housing for a portion of a substantially cylindrical valve stem 38. The valve body 36 includes a centrally formed opening 40 at a first end thereof, a centrally formed opening 42 at a second end thereof, and an axially extending bore 46 between the openings 40 and 42. An annular seal groove 44 is formed in the second end about the centrally formed opening 42. The bore 46 defines a metering chamber 48.

The valve stem 38 has a closed first end 38a and an open second end 38b. An axially extending passageway 50 extends from the open second end 38b to the closed first end 38a. A transverse bore 52 is formed through a wall of the valve stem 38 between the passageway 50 and an outside surface of the valve stem 38. The valve stem 38 also includes a circumferentially extending flange 54 defining a sealing surface 54a.

A first annular seal 56 is disposed in the seal groove 44 of the valve body 36. The valve stem 38 extends through the seal 56 and the stem opening 24 of the valve housing 22. The second end 38b of the valve stem 38 is mounted within the stem bore 32 of the valve block 26.

The metering valve 20 further includes a spring cage 58 having an annular base 60 and a substantially cylindrical spring cage portion 62 extending outwardly from the base 60 (extending upwardly when viewing FIGS. 2 and 3). The spring cage portion 62 defines a spring cage chamber 64. One or more fluid ports 62a are formed in the spring cage portion 62 and provide open and unrestricted fluid communication between the aerosol container 12 and the spring cage chamber 64. The annular base 62 of the spring cage 58 also includes a circumferentially extending flange 66.

The spring cage 58 has an axially extending bore 68 defining an annular seal groove 70 at one end of the bore 68 (an upper end of the bore 68 when viewing FIGS. 2 and 3). A second annular seal 72 is disposed in the seal groove 70 of the spring cage 58.

The metering valve 20 may include a substantially cylindrical spring guide 74 mounted within the spring cage chamber 64 of the spring cage 58. The spring guide 74 has a closed first end 74a and an open second end 74b. An axially extending passageway 76 extends from the open second end 74b to the closed first end 74a. Transverse bores 78 and 80 are formed through a wall of the spring guide 74 between the passageway 76 and an outside surface of the spring guide 74. The spring guide 74 also includes a circumferentially extending flange 82. A diameter of the opening 40 in the valve body 36 is larger than an outside diameter of the second end 74b of the spring guide, thus defining an annular fluid passageway 83 therebetween.

The spring guide 74 extends through seal 72 and the opening 40 in the valve body 36. The first end 38a of the valve stem 38 is mounted within the passageway 76 of the spring guide 74, thereby attaching the valve stem 38 to the spring guide 74.

Advantageously, the seal 56 acts to isolate the aerosol formulation in the aerosol container 12 from an exterior of the metering valve 20 by forming two types fluid tight seals: 1) an annular sliding seal between the seal 56 and the valve stem 38 where the valve stem 38 extends out of the valve housing 22, and 2) two compressive planar or face seals, one of which is defined between the valve body 36 and the seal 56, and a second of which is defined between the seal 56 and the valve housing 22.

Similarly, the seal 72 acts to isolate the aerosol formulation in the spring cage chamber 64 from the metering chamber 48 when the aerosol dispensing apparatus 10 is actuated, as described below, by also forming the two types fluid tight seals: 1) an annular sliding seal between the seal 72 and the spring guide 74, and 2) compressive planar or face seals between (a) the valve body 36 and the seal 72, and (b) the seal 72 and the spring cage 58.

The first end 74a of the spring guide 74 is disposed in a spring 84 that is disposed in the spring cage portion 62 of the spring cage 58. The spring 84 extends from a first end of the spring cage portion 62 to the flange 82 of the spring guide 74.

A third annular seal 86 may be disposed within an annular space 88 defined between the valve housing 22, the aerosol container 12, and the annular base 60 of the spring cage 58. Once the aerosol container 12 is mounted into the valve housing 22, the valve housing 22 may be crimped on the open end 12a of the aerosol container 12, as shown in FIG. 3. The aerosol container 12 is thus attached to the valve housing 22, and the seal 86 forms a fluid tight seal between the valve housing 22, the aerosol container 12, and the annular base 60 of the spring cage 58.

The battery 18 disposed within the battery housing 16 may be a conventional rechargeable battery, such as a 9 volt battery, although a non-rechargeable battery may also be used. The battery 18 is mounted within a conventional battery mount 90. A first electronic circuit board 92 is also mounted within the battery housing 16. The battery 18 is connected to the electronic circuit board 92 by electrical connectors 102, such as electrical wires. The circuit board 92 may have a microcontroller 94 and any other desired control electronics 96 for controlling the microvalve 30.

Figure 4:
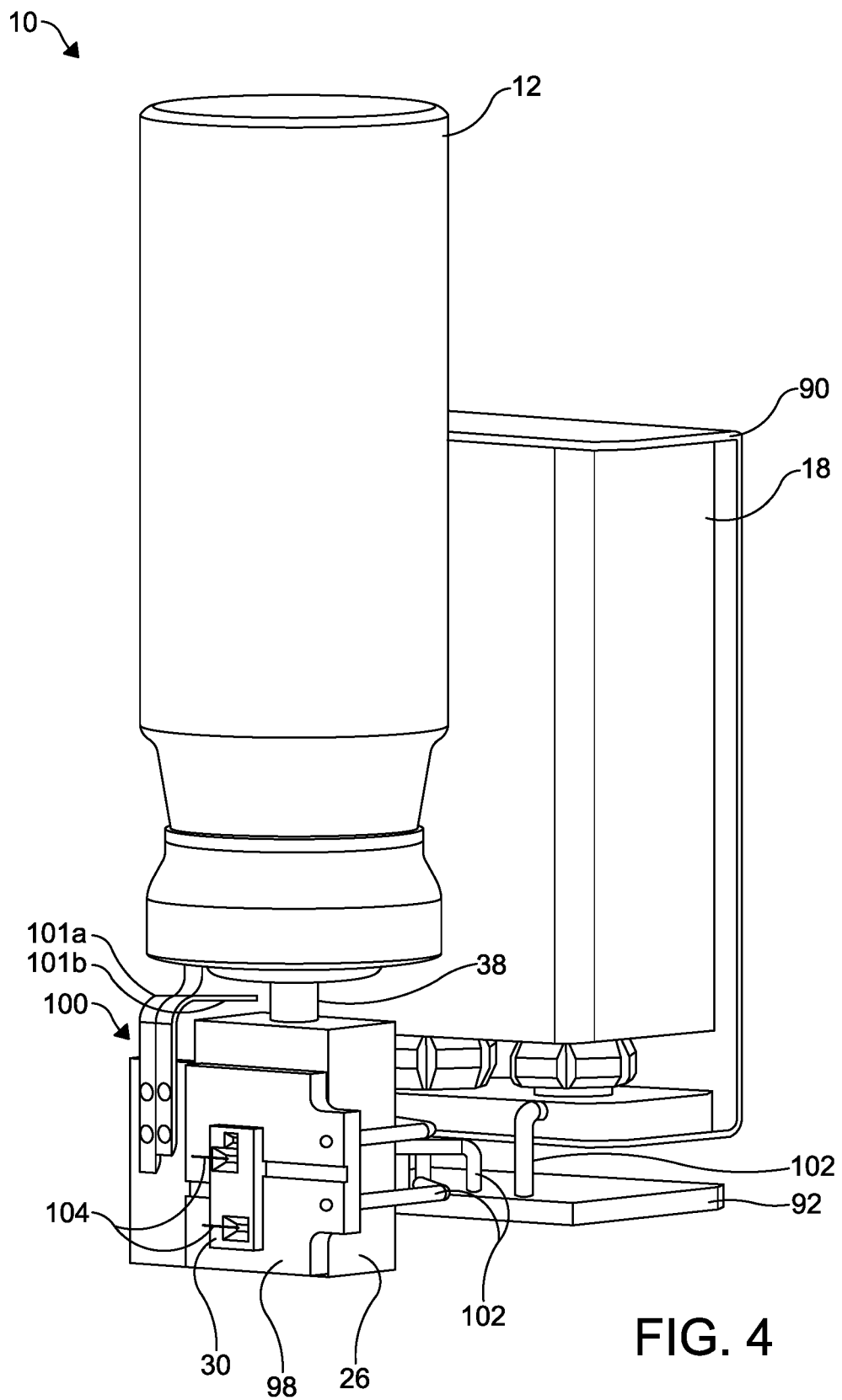
FIG. 4 is a perspective view of a portion of the improved aerosol dispensing apparatus illustrated in FIGS. 1 through 3 with the discharge piece and the battery housing removed for clarity.

As shown in FIGS. 2 through 4, a second circuit board 98 is mounted to an outside surface of the valve block 26. The circuit board 98 includes a microvalve mounting aperture 98a. An electronic switch 100 has a first portion 101a and a second portion 101b and is attached to the circuit board 98 to facilitate an electrical connection to the battery 18.

The microvalve 30 is mounted within the microvalve mounting aperture 98a and to an outside surface of the valve block 26, and is in fluid communication with the fluid passageway 34. Additional electrical connectors 102, such as electrical wires, extend between the first and second circuit boards 92 and 98.

Additional electrical wires 104 electrically connect the microvalve 30 to the second circuit board 98. As described in detail below in the description of the microvalve 30, the electrical wires 104 may extend from the second circuit board 98 through electrical ports, such as electrical ports 411, to bond pads 407a on the intermediate plate 403 for the purpose of passing an electrical current the microvalve 30.

In operation, the aerosol container 12 and the discharge piece 14 may be pushed toward one another, thus urging the valve stem 38 inwardly into the metering chamber 48 against the force of the spring 84. Aerosol formulation is then dispensed from the aerosol container 12 (downwardly when viewing FIGS. 2 and 3), through the metering valve 20, and through the microvalve 30. Aerosol formulation flow through the microvalve 30 may then be regulated and subsequently delivered through the discharge piece 14 to a patient. The discharge piece 14 directs the aerosol formulation toward the body cavity or skin area to which the formulation is to be delivered. For example, the discharge piece 14 may be configured with a mouthpiece 14a that can be inserted into the patient's mouth, thereby providing oral administration of the aerosol formulation.

Prior to the aerosol container 12 and the discharge piece 14 being pushed toward one another, aerosol formulation in the aerosol container 12 flows through the fluid port 62a, into the spring cage chamber 64, through the bore 78, the passageway 76, and into the bore 80. From the bore 80, the aerosol formulation passes through the annular passageway 83 into the metering chamber 48.

As the aerosol container 12 and the discharge piece 14 are pushed toward one another, the valve stem 38 is urged inwardly into the metering chamber 48, and bore 80 is moved past the seal 72 (upwardly when viewing FIGS. 2 and 3), thus preventing additional aerosol formulation from entering the metering chamber 48. Simultaneously, the bore 52 of the valve stem 38 is moved past the seal 56 (upwardly when viewing FIGS. 2 and 3) and into the metering chamber 48, thus creating a fluid flow path from the metering chamber 48 into the axially extending passageway 50 via the bore 52. In this position, the passageway 50 is in fluid communication with the microvalve 30 via the fluid passageway 34.

It will be understood however, that the metering valve 20 may be formed without the seal 72. In a valve otherwise similar to the metering valve 20, but without the seal 72, the valve 20 becomes an on-off valve wherein aerosol formulation may continuously flow from the aerosol container 12 to the passageway 50, even after the valve stem 38 has been urged inwardly into the metering chamber 48. In this embodiment (not shown) the microvalve 30 functions a metering valve to precisely control a dose amount of aerosol formulation dispersed from the aerosol dispensing apparatus 10.

As best shown in FIGS. 2 and 3, as the aerosol container 12 and the discharge piece 14 are pushed toward one another, the first portion 101a of the electronic switch 100 is urged into contact with the second portion 101b of the electronic switch 100, thus completing the electrical circuit and an actuating the microvalve 30.

The microcontroller 94 may be used to control a dose amount of aerosol formulation dispensed through the microvalve 30. The dose amount of aerosol formulation, measured by a volume or by a duration of a flow of an aerosol formulation dispensed through the microvalve 30, may be an amount predetermined and pre-programmed in the microcontroller 94, or may be an amount calculated by the microcontroller 94 based on input from sensors (not shown) within, or outside of, the aerosol dispensing apparatus 10.

The microcontroller 94 may also be used to keep track of a dose count. Additionally, the aerosol dispensing apparatus 10 may include a warning indicator (not shown) to notify the user when the aerosol dispensing apparatus 10 is nearing the end of its dose limit. The warning indicator may be any desired warning indicator, such as those that produce a visual or audible signal. It will be understood that the microcontroller 94 may be any desired microcontroller, or any similar device able to read data, perform limited calculations on that data, and control the function of the microvalve 30 based on the calculations performed.

Figure 8:
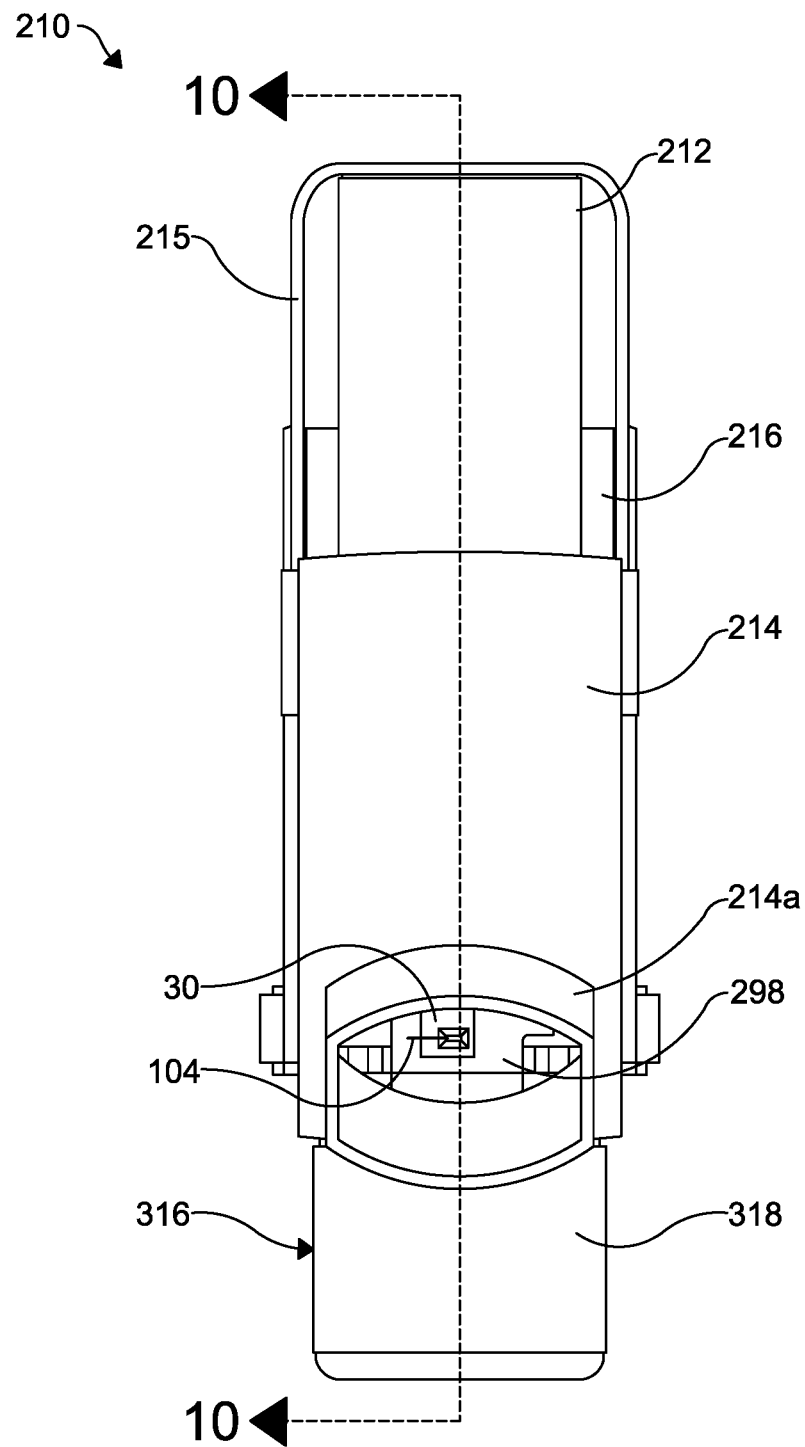
FIG. 8 is an elevational view of a second embodiment of an improved aerosol dispensing apparatus according to this invention.
Figure 9:
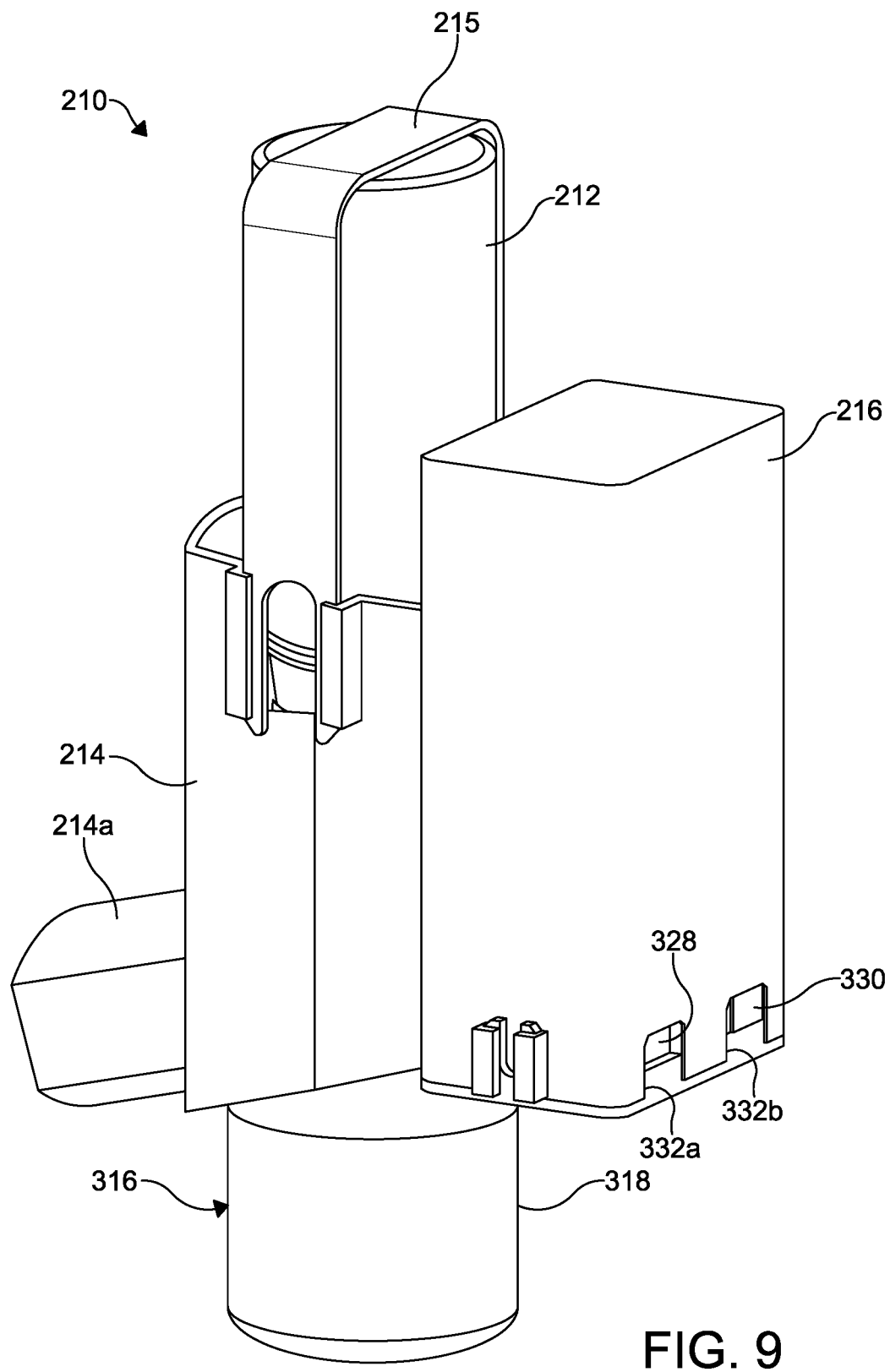
FIG. 9 is a perspective view of the second embodiment of the improved aerosol dispensing apparatus illustrated in FIG. 8.

One example of a known aerosol dispensing apparatus which may be modified to include the microvalve of this invention is a metered dose inhaler described in U.S. Pat. No. 7,748,378 to Hodson, the disclosure of which is incorporated herein in its entirety. FIGS. 1, 8, and 9 of U.S. Pat. No. 7,748,378 are reproduced in this application as FIGS. 5, 6, and 7, respectively. For the sake of brevity, only those portions of U.S. Pat. No. 7,748,378 that are particularly relevant to the present invention will be discussed herein.

Figure 5:
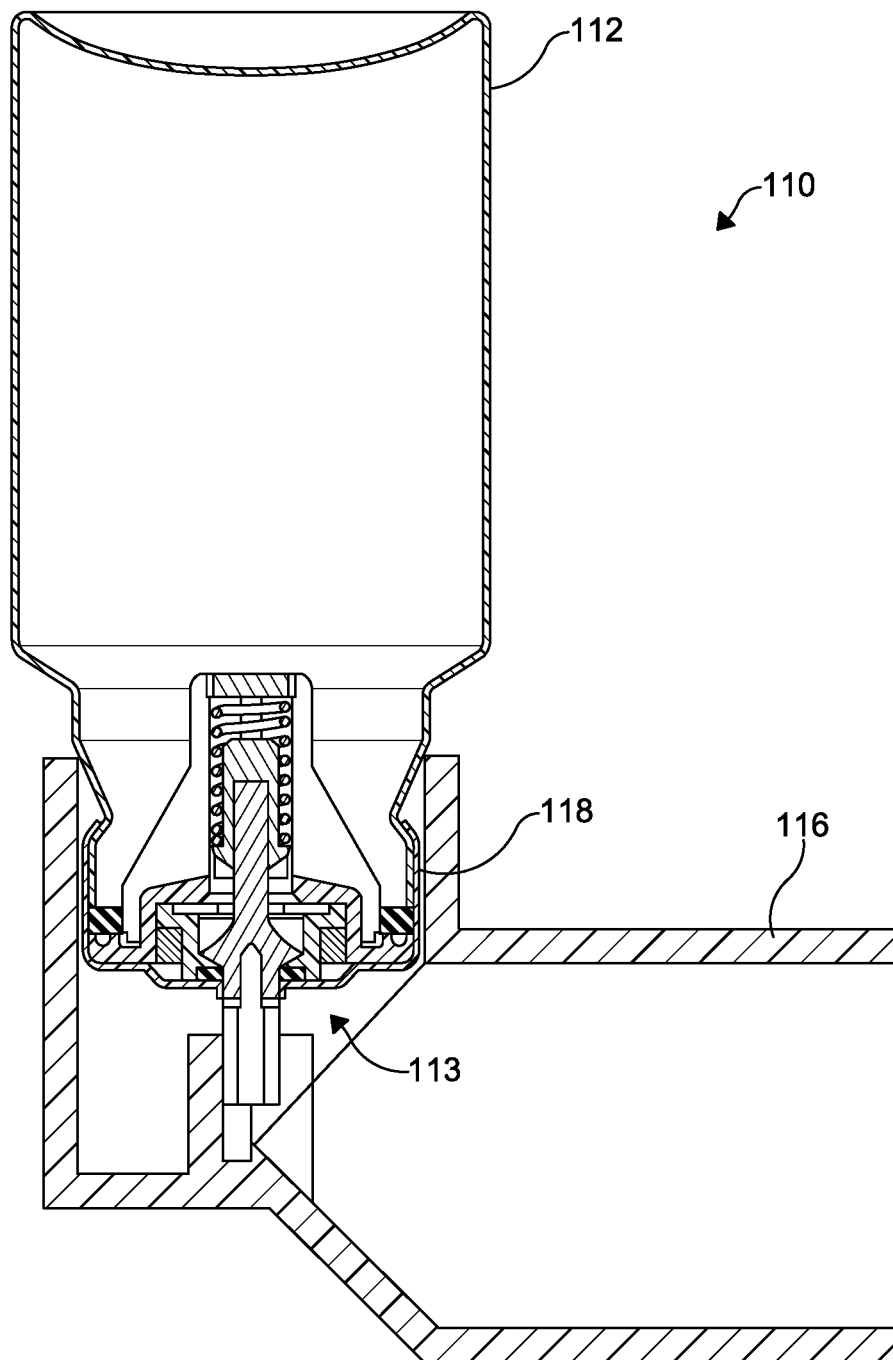
FIG. 5 is a cross-sectional elevational view of a conventional metered dose inhaler including a first embodiment of a conventional aerosol metering valve.

Referring to FIG. 5, a conventional aerosol dispensing apparatus is shown at 110. The aerosol dispensing apparatus 110 includes an aerosol container 112 mounted within a discharge piece 116. A first embodiment of a conventional metering valve 113 includes a valve housing 118. The valve housing 118 is attached at a first end thereof to the aerosol container 112 and at a second end thereof to the discharge piece 116.

Figure 6:
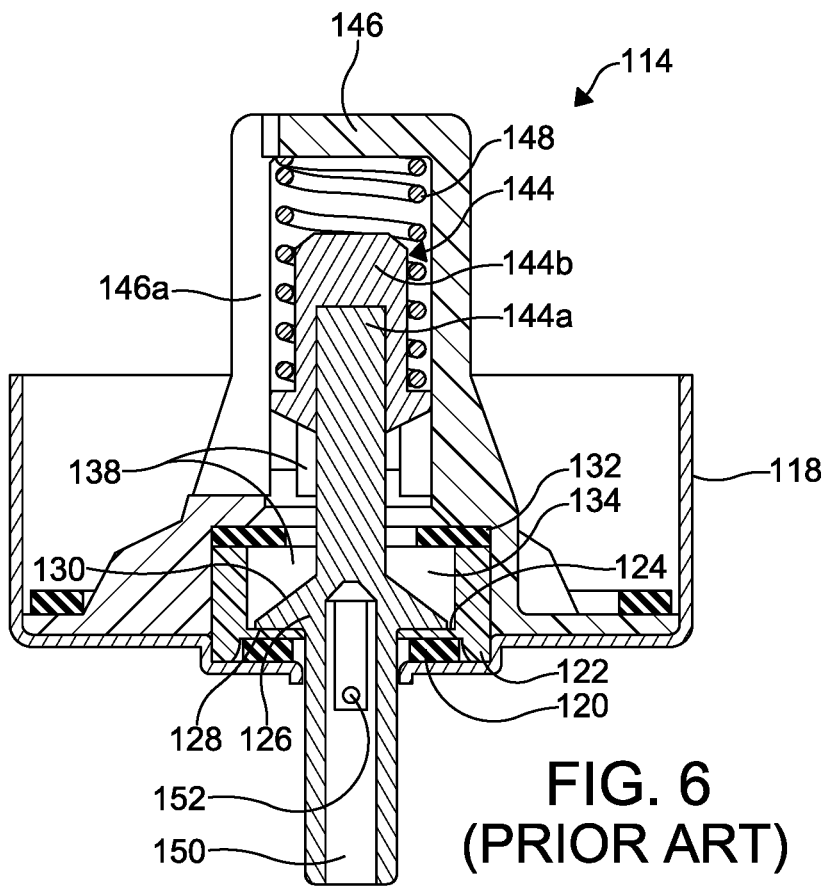
FIG. 6 is an enlarged cross-sectional elevational view a second embodiment of a conventional aerosol metering valve shown in the resting position.
Figure 7:
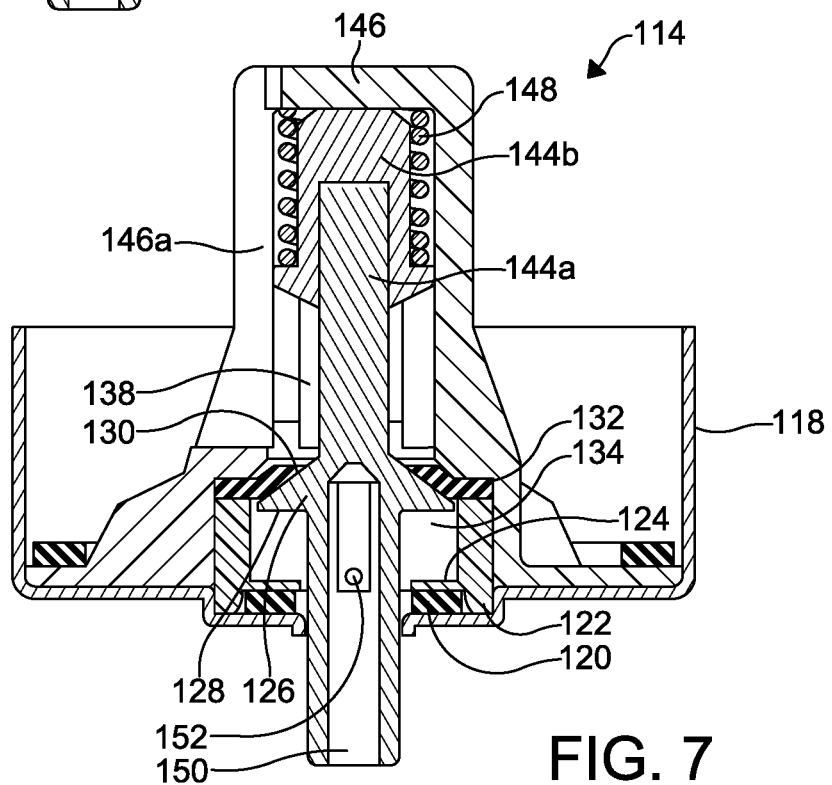
FIG. 7 is an enlarged cross-sectional elevational view of the conventional aerosol metering valve illustrated in FIG. 6 shown in the discharge stage position.

Referring now to FIGS. 6 and 7, a second embodiment of a conventional metering valve is shown at 114. The metering valve 114 may be used in the aerosol dispensing apparatus 110 and includes the valve housing 118 that is attached to the aerosol container 112. A valve body 122 is seated within the valve housing 118. The valve body 122 defines a housing for a valve stem 126. The valve body 122 also includes an interior surface 124 that defines an internal chamber or cavity of the valve body 122.

The valve stem 126 includes a passageway 150 through which a metered dose of an aerosol formulation is discharged. The passageway 150 may include one or more side holes 152. A radially outward extending portion of the valve stem 126 includes a metering surface 128 and a sealing surface 130.

The metering valve 114 further includes a spring cage 146 that, together with the valve body 122, defines an interior chamber 138 through which a portion of the valve stem 126 extends. One or more inlets 146a are formed in the spring cage 146 and provide open and unrestricted fluid communication between the interior chamber 138 and the aerosol container 112.

The metering valve 114 may include a spring guide 144 mounted on the end of the valve stem 126 and a spring 148 within the interior chamber 138. In the illustrated embodiment, the spring guide 144 is formed in two parts, a spring guide stem 144a, and a spring guide cap 144b.

The metering valve 114 also includes at least two annular gaskets or seals, including a seal 120 and a metering seal 132. The diaphragm 20 is positioned between the valve housing 118, the valve body 122, and the valve stem 126. The seal 120 isolates the aerosol formulation in the aerosol container 112 from the exterior of the metering valve 114 by forming two fluid tight seals: 1) an annular sliding seal between the seal 120 and the valve stem 126 where the valve stem 126 extends out of the valve housing 118, and 2) two compressive planar or face seals between the valve body 122, the seal 120, and the housing 118.

The metering seal 132 transiently isolates the aerosol formulation in a metering chamber 134, as best shown in FIG. 7, from the aerosol container 112 by forming a fluid-tight face seal between the metering seal 132 and the sealing surface 130 of the valve stem 126.

In operation, the aerosol container 112 and the discharge piece 116 are pushed toward one another, thus urging the valve stem 126 inwardly into the interior chamber 138 against the compressive force of the spring 148. Aerosol formulation is then dispensed from the aerosol container 112 (downwardly when viewing FIGS. 5 through 7), through the metering valve 114, then through the discharge piece 116 to a patient. The discharge piece 116 directs the aerosol formulation toward the body cavity or skin area to which the formulation is to be delivered. For example, the discharge piece 116 may be a mouthpiece that can be inserted into the patient's mouth, thereby providing oral administration of the aerosol formulation.

In the embodiment illustrated in FIGS. 5 through 7, aerosol formulation from the aerosol container 112 passes through the one or more of the inlets 146a and into the interior chamber 138 of the metering valve 114. From the interior chamber 138, the aerosol formulation passes between the valve stem 126 and the metering seal 132. Formulation flows around the proximal end of the valve stem 126 between the valve stem 126 and the interior surface of the valve body 124 and enters the metering chamber 134.

Thus, as the valve stem 126 is moved from a resting position, as shown in FIG. 6, to a discharge stage position, as shown in FIG. 7, aerosol formulation passes from the aerosol container 112 to the metering chamber 134 immediately upon actuation of the valve stem 126. Aerosol formulation continues to fill the metering chamber 134 until the metering valve 114 reaches the discharge stage position shown in FIG. 7.

As the valve stem 126 moves from the resting position to the discharge stage position, the metering seal 132 stretches such that contact surfaces of the metering seal 132 engage the sealing surface 130 and define a dynamic, reciprocating face seal. Additionally, one or more of the side holes 152 pass through the seal 120 and come into fluid communication with the metering chamber 134. The fluid communication thus established allows the aerosol formulation within the metering chamber 134 to be released through the discharge passageway 150 via the one or more of the side holes 152, thereby delivering a metered dose of aerosol formulation to the patient or other desired area.

When the valve stem 126 is in the discharge position, the flow path of aerosol formulation from the aerosol container 112 to the metering chamber 134 is cut off as the metering seal 132 contacts the sealing surface 130 of the valve stem 126, as shown in FIG. 3. The metering seal 132 forms a fluid-tight face seal with the sealing surface 130, thereby concluding filling of the metering chamber 134 and isolating the metering chamber 134 prior to discharge. At this stage, the metered dose of aerosol formulation is isolated and ready for discharge from the metering chamber 134 and delivery to the patient.

A conventional metering valve, such as the metering valve 114, may be used to administer virtually any aerosol formulation of drugs, in the form of a dispersant into a body cavity or onto the skin of a patient. Such conventional metering valves however, are not limited to medicinal applications, and may be used whenever a specific amount of pressurized fluid is desired to be delivered to a specific location.

Referring now to FIGS. 8 through 13, a second embodiment of an improved aerosol dispensing apparatus is shown at 210. The aerosol dispensing apparatus 210 includes an aerosol container 212 mounted within a discharge piece 214. The discharge piece 214 may be configured with a mouthpiece 214a that can be inserted into the patient's mouth, thereby providing oral administration of an aerosol formulation. A battery housing 216 is attached to the discharge piece 214 and contains a battery 218.

Figure 10:
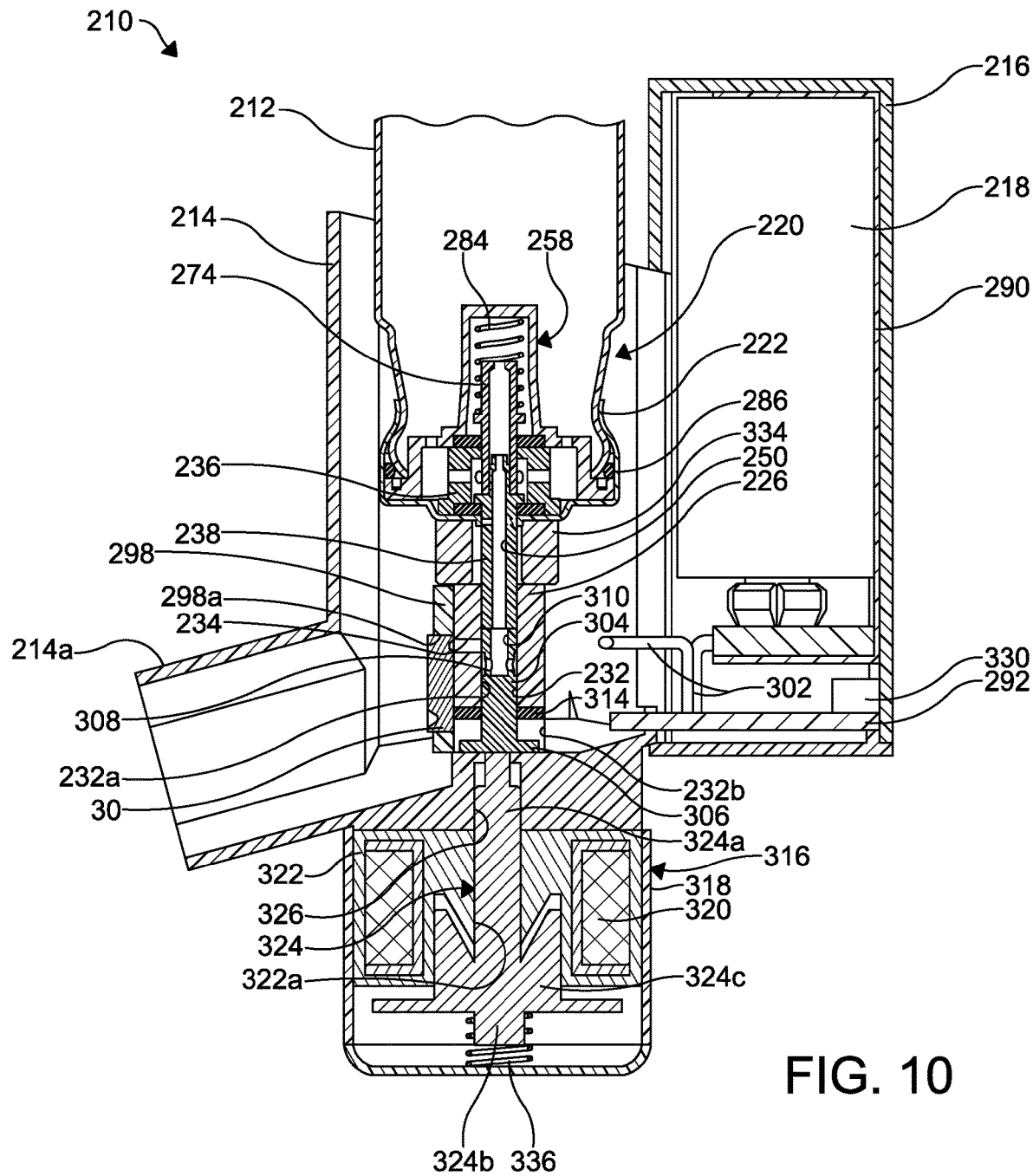
FIG. 10 is a cross-sectional elevational view of the second embodiment of the improved aerosol dispensing apparatus taken along the line 10-10 of FIG. 8.
Figure 11:
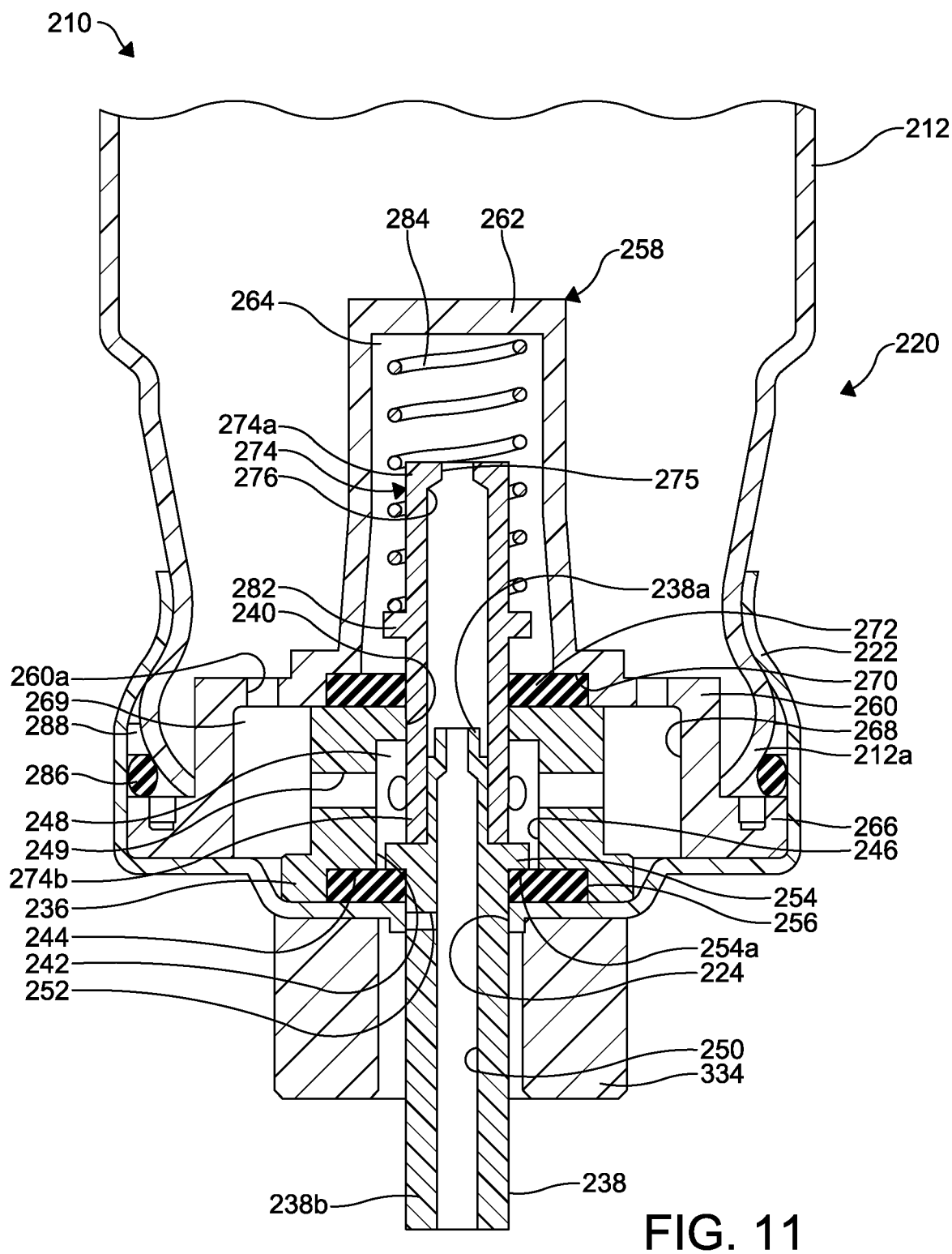
FIG. 11 is an enlarged cross-sectional view of a first portion of the second embodiment of the improved aerosol dispensing apparatus illustrated in FIG. 10.
Figure 12:
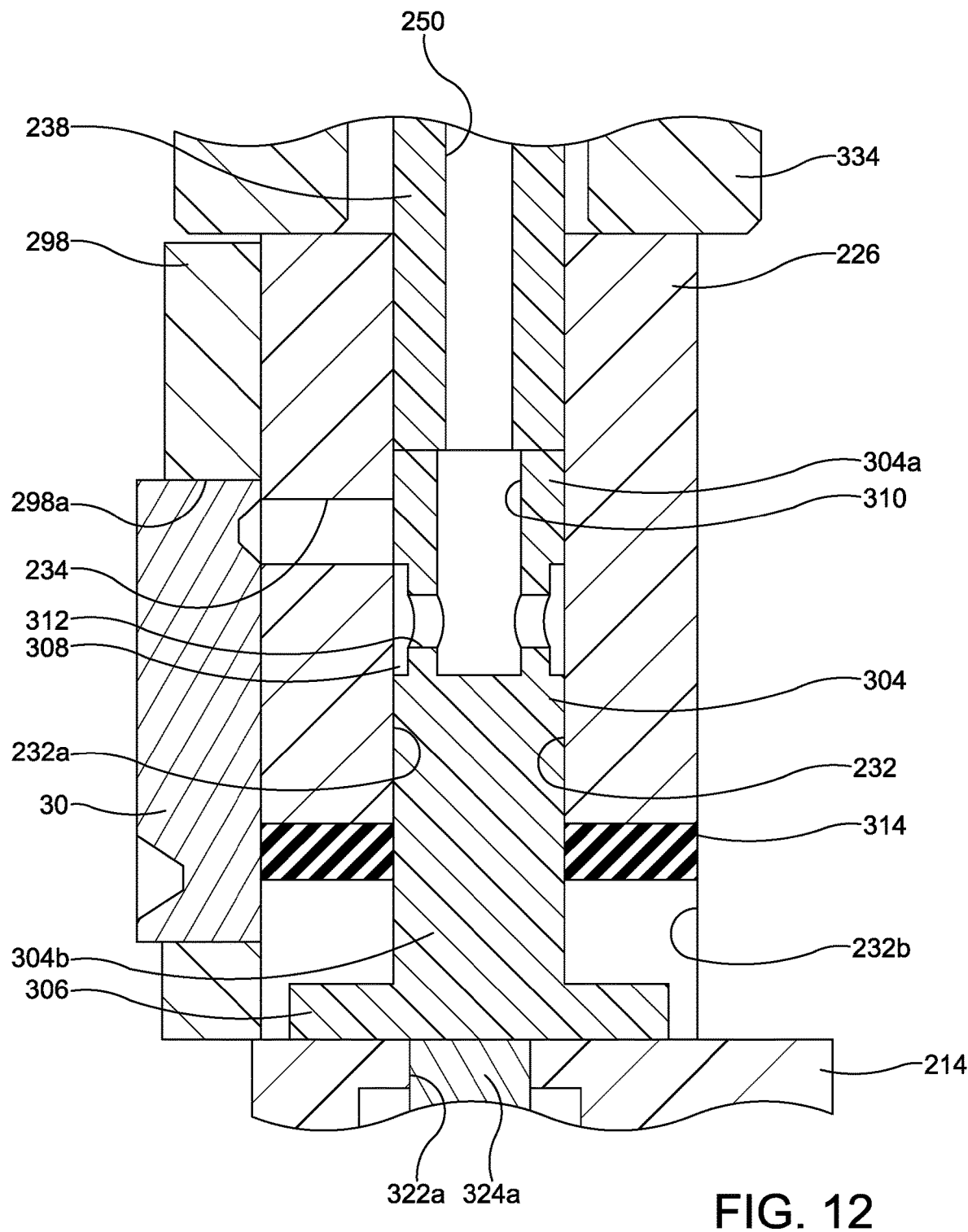
FIG. 12 is an enlarged cross-sectional view of a second portion of the second embodiment of the improved aerosol dispensing apparatus illustrated in FIG. 10.
Figure 13:
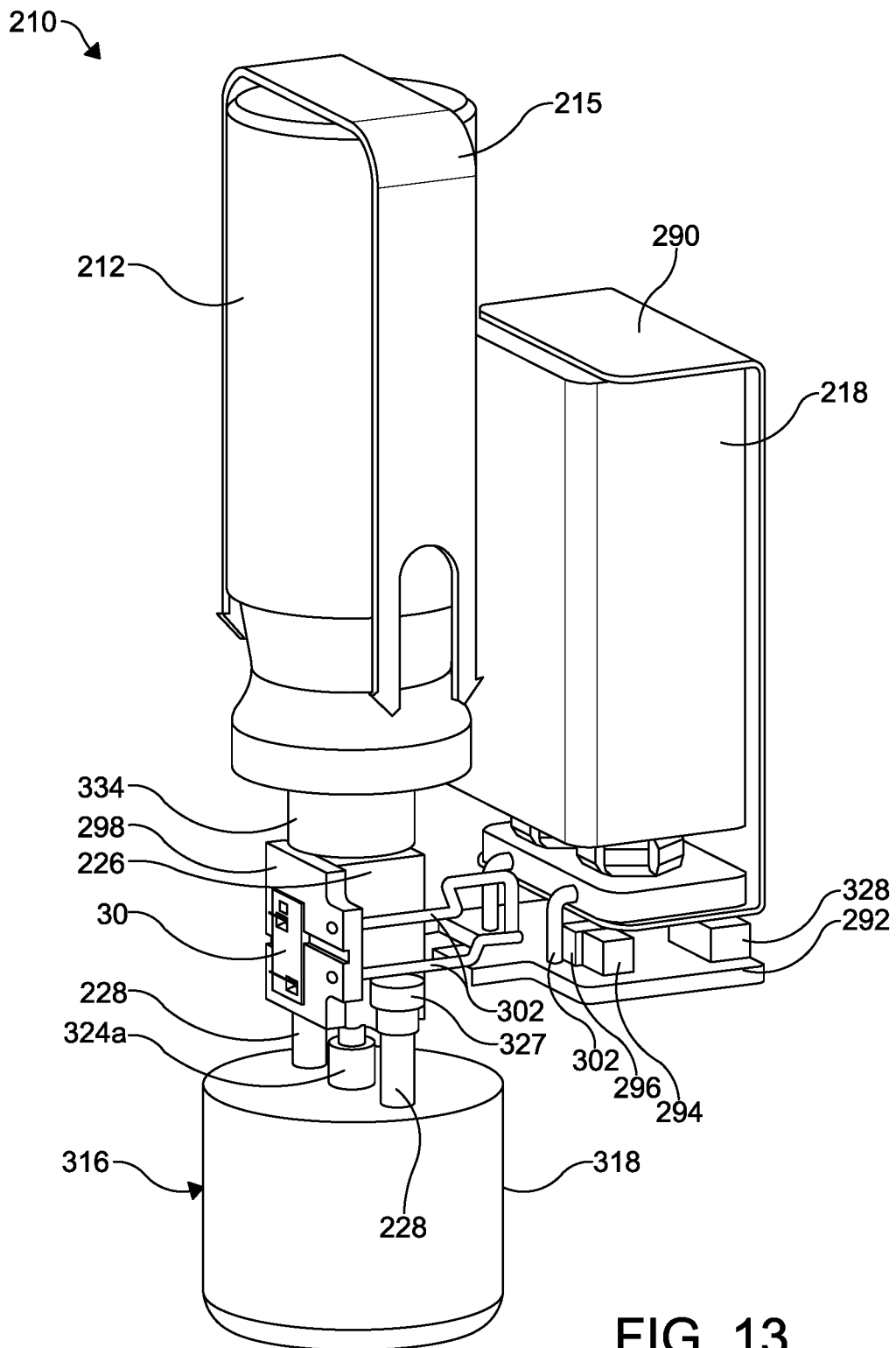
FIG. 13 is a perspective view of a portion of the second embodiment of the improved aerosol dispensing apparatus illustrated in FIGS. 8 through 12 with the discharge piece and the battery housing removed for clarity.

As best shown in FIGS. 10 through 12, a flow control valve is shown at 220. The flow control valve 220 is configured as an on-off valve and includes a substantially cup-shaped valve housing 222 having a centrally formed stem opening 224 formed in a bottom surface thereof. A first or open end of the valve housing 222 is attached to an open end 212a of the aerosol container 212 such as by crimping. Alternatively, the valve housing 222 may be attached to the aerosol container 212 by other means, such as with an adhesive, with a laser weld, and with an electronic beam weld.

The aerosol container 212 may further be retained in the discharge piece 214 by a retaining strap 215 (see FIGS. 8, 9, and 13) that is removably attached to the discharge piece 214 on opposite sides thereof.

A valve block 226 is mounted to an inside surface of the discharge piece 214 by any desired means, such as by one or more threaded fasteners 228 (shown in FIG. 13) or with an adhesive. The valve block 226 includes an axially extending stepped bore 232 formed therethrough. The stepped bore 232 has first diameter portion 232a and a second diameter portion 232b, wherein the first diameter portion 232a is smaller than the second diameter portion 232b. The valve block 226 also includes a transverse fluid passageway 234 that is in fluid communication with the microvalve 30. The valve block 226 may include mounting tabs 227, best shown in FIG. 13 for attaching the valve block 226 to a portion of the discharge piece 214.

An electronically actuated metering valve is mounted to an outside surface of the valve block 226. In the illustrated embodiment, the metering valve is an electronically actuated microvalve 30, the structure and function of which is described below. Alternatively, the metering valve may be any relatively small; i.e., able to fit within the discharge piece 214, electronically controlled flow control valve, such as a solenoid valve.

The flow control valve 220 further includes a valve body 236 seated within the valve housing 222. The valve body 236 is substantially cylindrical in shape and defines a housing for a portion of a substantially cylindrical valve stem 238. The valve body 236 includes a centrally formed opening 240 at a first end thereof, a centrally formed opening 242 at a second end thereof, and an axially extending bore 246 between the openings 240 and 242. An annular seal groove 244 is formed in the second end about the centrally formed opening 242. The bore 246 defines a fluid chamber 248. One or more transverse fluid openings 249 are formed in the valve body 236.

The valve stem 238 has a first end 238a and a second end 238b. An axially extending passageway 250 extends from the first end 238a to the second end 238b. A transverse bore 252 is formed through a wall of the valve stem 238 between the passageway 250 and an outside surface of the valve stem 238. The valve stem 238 also includes a circumferentially extending flange 254 defining a sealing surface 254a.

A first annular seal 256 is disposed in the seal groove 244 of the valve body 236. The valve stem 238 extends through the seal 256 and the stem opening 224 of the valve housing 222. The second end 238b of the valve stem 238 is slidably mounted within the first diameter portion 232a of the stepped bore 232 of the valve block 226.

The flow control valve 220 further includes a spring cage 258 having an annular base 260 and a substantially cylindrical spring cage portion 262 extending outwardly from the base 260 (extending upwardly when viewing FIGS. 10 and 11). The spring cage portion 262 defines a spring cage chamber 264. The annular base 262 of the spring cage 258 also includes a circumferentially extending flange 266.

The spring cage 258 has an axially extending bore 268 defining an annular seal groove 270 at one end of the bore 268 (an upper end of the bore 268 when viewing FIGS. 10 and 11). The bore 268 defines a fluid chamber 269. A second annular seal 272 is disposed in the seal groove 270 of the spring cage 258. One or more fluid ports 260a are formed in the spring cage base 260 and provide open and unrestricted fluid communication between the aerosol container 212 and the fluid chamber 269.

The flow control valve 220 may include a substantially cylindrical spring guide 274 mounted within the spring cage chamber 264 of the spring cage 258 and extending into the valve body 236. The spring guide 274 has a first end 274a having an axially extending opening 275 formed therein, and an open second end 274b. An axially extending passageway 276 extends from the open second end 274b to the first end 274a. The spring guide 74 also includes a circumferentially extending flange 282.

The spring guide 274 extends through the seal 272 and the opening 240 in the valve body 236. The first end 238a of the valve stem 238 is mounted within the in the passageway 276 of the spring guide 274, thereby attaching the valve stem 238 to the spring guide 274.

The seal 256 acts to isolate the aerosol formulation in the aerosol container 212 from an exterior of the flow control valve 220 by forming an annular sliding seal between the seal 256 and the valve stem 238 where the valve stem 238 extends out of the valve housing 222. The seal 256 also forms two compressive planar or face seals, one of which is defined between the valve body 236 and the seal 256, and a second of which is defined between the seal 256 and the valve housing 222. Similarly, the seal 272 acts to isolate the aerosol formulation in the fluid chamber 248 from the spring cage chamber 264.

The first end 274a of the spring guide 274 is disposed in a spring 284 that is disposed in the spring cage portion 262 of the spring cage 258. The spring 284 extends from a first end of the spring cage portion 262 to the flange 282 of the spring guide 274.

A third annular seal 286 may be disposed within an annular space 288 defined between the valve housing 222, the aerosol container 212, and the annular base 260 of the spring cage 258. Once the aerosol container 212 is mounted into the valve housing 222, the valve housing 222 may be crimped on the open end 212a of the aerosol container 212, as shown in FIG. 11. The aerosol container 212 is thus attached to the valve housing 222, and the seal 286 forms a fluid tight seal between the valve housing 222, the aerosol container 212, and the annular base 260 of the spring cage 258.

Referring again to FIGS. 10 and 12, a substantially cylindrical push rod 304 has an open first end 304a and a closed second end 304b. The push rod 304 also includes a circumferentially extending flange 306 at the second end 304b thereof and a circumferentially extending groove 308 formed in an outside surface thereof. An axially extending passageway 310 extends from the open first end 304a to at least one transverse fluid opening 312 formed through a wall of the push rod 304. The transverse fluid opening 312 extends from the axially extending passageway 310 to the circumferentially extending groove 308. The first end 304a of the push rod 304 is slidably mounted within the first diameter portion 232a of the stepped bore 232 of the valve block 226. The second end 304b of the push rod 304 is urged against a surface of the discharge piece 214.

An annular spacer 334 is mounted between the annular base 222 and the valve block 226, and around the valve stem 238.

A fourth annular seal 314 is disposed in the second diameter portion 232b of the stepped bore 232, such that the push rod 304 extends through the seal 314.

A solenoid 316 is mounted to an outside surface of the discharge piece 214 (a lower surface when viewing FIG. 10), and includes a solenoid housing 318. A solenoid coil 320 is mounted in a coil body 322. An axially moveable plunger 324 is slidably mounted within an axially extending bore 322a formed through the coil body 322. The plunger 324 includes a substantially cylindrical first end 324a, a central portion 324c, and a substantially cylindrical second end defining a spring attachment member 324b. The first end 324a extends outwardly (upwardly when viewing FIG. 10) through a passageway 326 formed in opening in the discharge piece 214 and engages the push rod 304. The plunger 324 is retained in an unactuated position, as shown in FIG. 10, by a spring 336 that is attached to the solenoid housing 318 and to the spring attachment member 322b. Electrical connectors (not shown), such as electrical wires, extend between the battery 218 and the solenoid 316.

The battery 218 disposed within the battery housing 216 may be any conventional rechargeable or non-rechargeable battery, such as the battery 18 described above in the dispensing apparatus 10. The battery 218 is mounted within a conventional battery mount 290. A first electronic circuit board 292 is also mounted within the battery housing 216. The battery 218 is connected to the electronic circuit board 292 by electrical connectors 302, such as electrical wires. The circuit board 292 may have a microcontroller 294, a communications or charging port 328, an actuator switch 330, and any other desired control electronics 296 for controlling the microvalve 30. Access openings 332a and 332b are formed in the battery housing 362 to provide access to the charging port 328 and the actuator switch 330, respectively.

As shown in FIGS. 10 through 13, a second circuit board 298 is mounted to an outside surface of the valve block 226. The circuit board 298 includes a microvalve mounting aperture 298a.

The microvalve 30 is mounted within the microvalve mounting aperture 298a and to an outside surface of the valve block 226, and is in fluid communication with the fluid passageway 234. Additional electrical connectors 302, such as electrical wires, extend between the first and second circuit boards 292 and 298.

The electrical wires 104 electrically connect the microvalve 30 to the second circuit board 298. As described in detail below in the description of the microvalve 30, the electrical wires 104 may extend from the second circuit board 298 through electrical ports, such as electrical ports 411, to bond pads 407*a* on the intermediate plate 403 for the purpose of passing an electrical current the microvalve 30.

To operate the improved aerosol dispensing apparatus 210, a user may actuate the solenoid 316 by engaging the actuator switch 330. Upon actuation, the solenoid plunger 324 is urged outwardly against the push rod 304 (upwardly when viewing FIGS. 10 and 12), thus also urging the push rod 304, the valve stem 238, and the spring guide 274 upwardly until the transverse bore 252 is positioned within the fluid chamber 248 and the groove 308 and the fluid openings 312 are aligned with the fluid passageway 234.

In this actuated position, fluid, such as an aerosol formulation, in the aerosol container 212 may flow through the fluid ports 260*a*, which define a first flow path, into the fluid chamber 269, through the fluid openings 249, which define a second flow path, and into the fluid chamber 248. Because the transverse bore 252 is positioned within the fluid chamber 248 and the groove 308 and the fluid openings 312 are aligned with the fluid passageway 234, the aerosol formulation may then flow through the bore 252, defining a third fluid flow path, and to the microvalve 30 via the passageway 250, the fluid openings 312, and the fluid passageway 234. Aerosol formulation flow through the microvalve 30 may then be regulated and subsequently delivered through the discharge piece 214 to the patient or other desired location, as described below.

Thus, when the improved aerosol dispensing apparatus 210 is actuated by the user, a continuous flow of aerosol formulation travels through the flow control valve 220 to the microvalve 30. The flow of aerosol formulation through the microvalve 30, and therefore the dose amount of aerosol formulation dispersant dispensed thereby, may then be very precisely controlled by the microcontroller 294 as required for a desired treatment.

The microcontroller 294 may include an algorithm that moves the microvalve 30 between open and closed positions to ensure optimal dispersal of the aerosol formulation to a user. For example, by selectively moving the microvalve 30 between open and closed positions, the microcontroller 294 may precisely control dosage volume and/or the duration of an aerosol formulation dose through the microvalve 30. An optimal dosage volume and an optimal duration of an aerosol formulation dose will vary based on factors including the type of medication being dispersed, the age of the user, and the like, and may be determined by routine experimentation.

The microcontroller 294 may also include an algorithm with a counter function configured to count the number of doses administered in a given time period, such as the elapsed time since the most recent previous aerosol container 212 change. The microcontroller 294 may also be programmed as needed by a physician or a pharmacist via the communications port 328.

The improved aerosol dispensing apparatus 210 therefore advantageously eliminates the need for the user to depress the aerosol container 212 in a conventional manner to initiate the flow of dispersant, such as the aerosol formulation.

Micro Electro Mechanical Systems (MEMS) are a class of systems that are physically small, having features with sizes in the micrometer range; i.e., about 10 μm or smaller. These systems have both electrical and mechanical components. The term "micromachining" is commonly understood to mean the production of three-dimensional structures and moving parts of MEMS devices. MEMS originally used modified integrated circuit (computer chip) fabrication techniques (such as chemical etching) and materials (such as silicon semiconductor material) to micromachine these very small mechanical devices. Today, there are many more micromachining techniques and materials available. The term "micromachined device" as used in this application means a device having some features with sizes of about 10 μm or smaller, and thus by definition is at least partially formed by micromachining. More particularly, the term "microvalve" as used in this application means a valve having features with sizes of about 10 μm or smaller, and thus by definition is at least partially formed by micromachining. The term "microvalve device" as used in this application means a micromachined device that includes a microvalve, and that may include other components. It should be noted that if components other than a microvalve are included in the microvalve device, these other components may be micromachined components or standard sized (larger) components. Similarly, a micromachined device may include both micromachined components and standard sized (larger) components.

Various microvalve devices have been proposed for controlling fluid flow within a fluid circuit. A typical microvalve device includes a displaceable member or valve component movably supported by a body for movement between a closed position and a fully open position. When placed in the closed position, the valve component substantially blocks or closes a first fluid port that is otherwise in fluid communication with a second fluid port, thereby substantially preventing fluid from flowing between the fluid ports. When the valve component moves from the closed position to the fully open position, fluid is increasingly allowed to flow between the fluid ports.

U.S. Pat. Nos. 6,523,560, 6,540,203, and 6,845,962, the disclosures of which are incorporated herein by reference, describe microvalves made of multiple layers of material. The multiple layers are micromachined and bonded together to form a microvalve body and the various microvalve components contained therein, including an intermediate mechanical layer containing the movable parts of the microvalve. The movable parts are formed by removing material from an intermediate mechanical layer (by known micromachined device fabrication techniques, such as, but not limited to, Deep Reactive Ion Etching) to create a movable valve element that remains attached to the rest of the part by a spring-like member. Typically, the material is removed by creating a pattern of slots through the material to achieve the desired shape. The movable valve element will then be able to move in one or more directions an amount roughly equal to the slot width.

Although the surface area of the intermediate mechanical layer in each of the microvalves disclosed in U.S. Pat. Nos. 6,523,560, 6,540,203, and 6,845,962 is relatively small, e.g. about 52 $mm^2$, it is desirable to provide an intermediate mechanical layer for a microvalve having an even smaller surface area.

One embodiment of a microvalve device suitable for use with the invention is described in U.S. Patent Application Publication No. 2014/0373937 to Fuller et al. published Dec. 25, 2014 and incorporated in its entirety herein. FIGS.

1 through 5 of U.S. Patent Application Publication No. 2014/0373937 are reproduced in this application as FIGS. 14 through 18, respectively. For the sake of brevity, only those portions of U.S. Patent Application Publication No. 2014/0373937 that are particularly relevant to the present invention will be discussed here.

Figure 14:
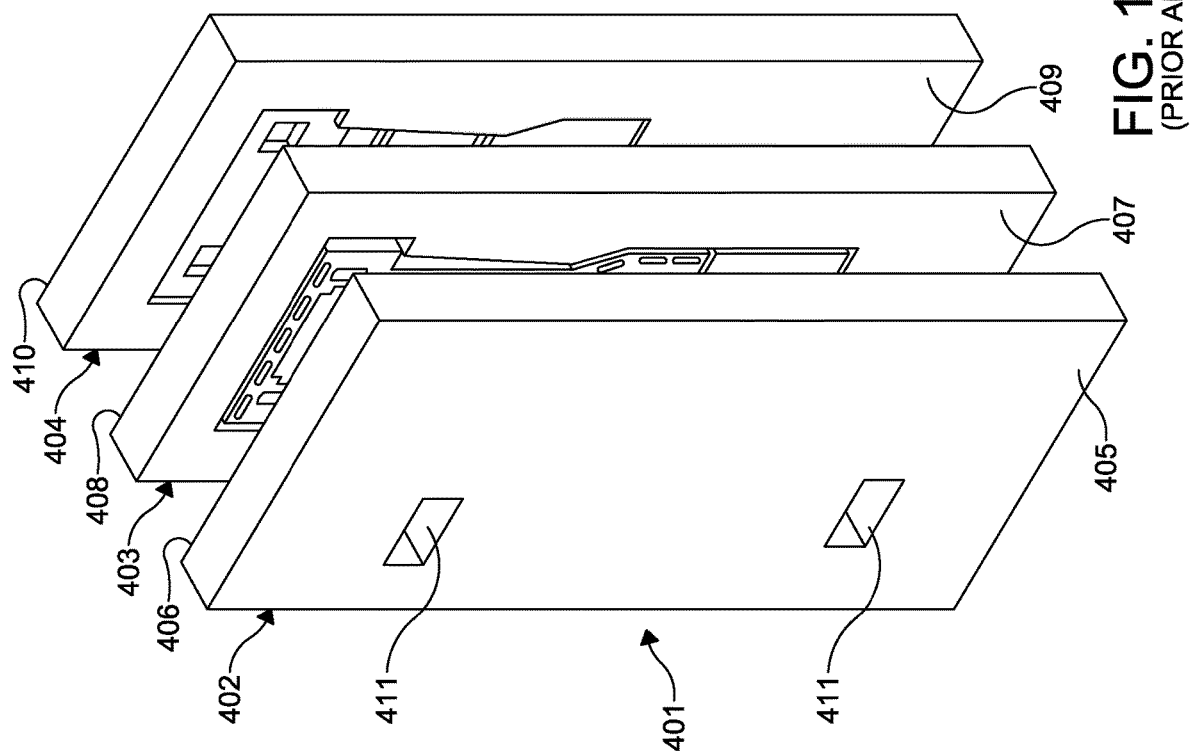
FIG. 14 is an exploded perspective view of a known microvalve device having a cover plate, an intermediate plate, and a base plate.

FIG. 14 is an exploded perspective view of a conventional microvalve 401. The microvalve device 401 has a cover plate 402, an intermediate plate 403, and a base plate 404. The cover plate 402 has an outer surface 405 and an inner surface 406. The intermediate plate 403 has a first surface 407 and a second surface 408. The base plate 404 has an inner surface 409 and an outer surface 410. The cover plate 402, the intermediate plate 403, and the base plate 404 combine to define a body configured to support a valve element, described below.

Figure 15:
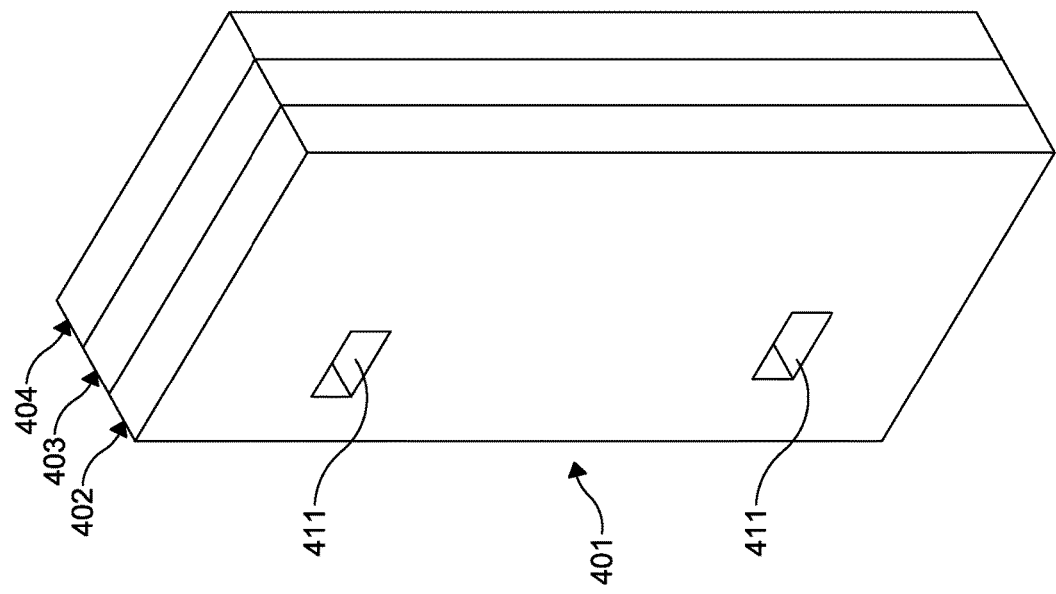
FIG. 15 is a perspective view of the known microvalve device illustrated in FIG. 14 shown assembled.

FIG. 15 is a perspective view of the microvalve 401 illustrated in FIG. 14 shown assembled. Upon assembly of the microvalve 401, the inner surface 406 of the cover plate 402 engages the first surface 407 of the intermediate plate 403, while the inner surface 409 of the base plate 404 engages the second surface 408 of the intermediate plate 403.

The cover plate 402, the intermediate plate 403, and/or the base plate 404 of the microvalve 401 may be chemically and/or physically bonded together by any suitable method known to those of ordinary skill in the art, non-limiting examples of which include one or more types of mechanical fasteners and/or adhesives.

The inner surface 406 of the cover plate 402 is shown in FIG. 16. In the illustrated embodiment, the cover plate 402 includes electrical ports 411, the purpose of which is described below.

As shown in FIG. 16, the inner surface 406 of the cover plate 402 includes an actuator cavity 412 having one or more pressure equalization recesses or depressions 413 that reduce or prevent pressure imbalances during operation of the microvalve 401.

The actuator cavity 412 in the inner surface 406 of the cover plate 402 is located adjacent to, and has a shape corresponding to, an actuator 414 on the intermediate plate 403.

The illustrated actuator cavity 412 includes an upper actuator arm cavity region 412a, a central actuator arm cavity region 412b, a lower actuator arm cavity region 412c, a dead end rib cavity region 412d, a central rib cavity region 412e, and an open end rib cavity region 412f.

The electrical ports 411, the actuator cavity 412, and the one or more pressure equalization recesses 413 in the inner surface 406 of the cover plate 402 may be formed by any suitable process known to those of ordinary skill in the art, a non-limiting example of which includes an etching process.

As shown in FIG. 17, the actuator 414 includes a plurality of actuator ribs 415 having a dead end rib region 416, an open end rib region 417, and a central rib region 418 joined in a herringbone pattern to a moveable central spine 419, and a displaceable actuator arm 420 operatively coupled to the spine 419. The intermediate plate 403 may also include one or more air flow passages 421 for purging air from the open end rib region 417 of the plurality of actuator ribs 415 and out of the microvalve 401.

The actuator arm 420, which is operatively coupled to the spine 419, includes a pivot anchor or hinge 422 that bends or flexes to accommodate movement of the actuator arm 420 as it is arcuately displaced between actuated and un-actuated positions by movement of the spine 419 of the actuator 414.

The arcuate movement of the actuator arm 420 occurs in and defines a plane that is parallel to the first surface 407 in the regions where the first surface 407 contacts the cover plate 402 and/or a plane that is parallel to the second surface 408 in the regions where the second surface 408 contacts the base plate 404. The actuator arm 420 also includes a valve element 423 having slots 424 and 425 for controlling the flow of a fluid through the microvalve 401, and a plurality of pressure equalization openings 426 for reducing or preventing pressure imbalances so as to minimize or prevent "out of plane" movement of the valve element 423 of the actuator arm 420 during actuation and un-actuation thereof.

The first surface 407 of the intermediate plate 403 may also include bond pads 407a arranged in bond pad regions which are located adjacent to the electrical ports 411 of the cover plate 402 when the microvalve 401 is assembled. Upon assembly of the microvalve 401, the bond pads 407a provide an electrical contact between electrical wires (not shown) bonded to the bond pads 407a and connected to a source of electrical power (not shown) and the plurality of actuator ribs 415 of the intermediate plate 403 for the purpose of passing an electrical current through the plurality of actuator ribs 415 during actuation or energization.

The inner surface 409 of the base plate 404 is shown in FIG. 18. In the illustrated embodiment, the base plate 404 includes a plurality of fluid ports for permitting passage of fluid through the microvalve 401, including a normally open fluid port 427, a normally closed fluid port 428, and a common fluid port 429. It will be understood however, that each of the respective fluid ports may be configured to be either normally opened or normally closed in the absence or presence of an electrical current passing through the plurality of actuator ribs 415.

When the intermediate plate 403 is assembled with the base plate 404, and the actuator arm 420 and the valve element 423 of the actuator 414 have not been actuated, the normally open fluid port 427 is in an open position and the normally closed fluid port 428 is in a closed position. In the open position, the slot 424 is positioned such that it overlaps a portion of the normally open fluid port 427, thereby allowing fluid flow between the normally open fluid port 427 and the common fluid port 429. When the normally closed fluid port 428 is in the closed position, the slot 425 is positioned away from the fluid port 428, thereby substantially preventing fluid flow between the fluid port 428 and the common fluid port 429.

During actuation of the microvalve 401, the ribs 415 are heated by passing an electrical current therethrough. The ribs 415 then undergo thermal expansion and elongate, which urges the spine 419 and the attached actuator arm 420 away from the ribs 415 (to the right when viewing FIG. 17). The actuator arm 420 then bends or flexes at the hinge 422 to accommodate movement of the spine 419 thereby causing the valve element 423, and its slots 424 and 425 to move in the plane of normal motion along an arcuate path (to the right when viewing FIG. 17) to a stressed position which closes the normally open fluid port 427 and opens the normally closed fluid port 428.

When the electrical current is removed from the ribs 415, the ribs 415 cool and contract, urging the central spine 419 back toward the ribs 415 (to the left when viewing FIG. 17). The actuator arm 420 and valve element 423 then return to the un-actuated position, wherein the normally open fluid port 427 is again open, and the normally closed fluid port 428 is again closed.

The embodiment of the microvalve 401 illustrated in FIGS. 14 through 18 is packaged in a conventional U-flow configuration, wherein the fluid ports 427, 428, and 429 are located on the same side (the base plate 404 side) of the microvalve 401. Alternatively, the microvalve 401 may be packaged in a conventional through-flow configuration, wherein at least the fluid inlet and the fluid outlet are located on opposite sides (on the cover plate 402 and the base plate 404 sides) of the microvalve 401. The structure and manner of operation of such a through-flow configured microvalve may be otherwise similar to the embodiment of the microvalve 401 described herein.

Another embodiment of a microvalve device suitable for use with the invention is the silQflo™ silicon servo valve manufactured by DunAn Microstaq, Inc. and illustrated on their website at www.dmq-us.com. Other microvalves may also be used with the aerosol dispensing apparatus and associated metering valves and flow control valves disclosed herein.

It will be understood that the microvalve 30 may be used with other metering valves, such as the metering valve 113, shown in FIG. 5, and the metering valve 114, shown in FIGS. 6 and 7, to regulate or modify the flow of the aerosol formulation in an aerosol dispensing apparatus.

The principle and mode of operation of the invention have been described in its preferred embodiments. However, it should be noted that the invention described herein may be practiced otherwise than as specifically illustrated and described without departing from its scope.

What is claimed is:

1. An aerosol dispensing apparatus comprising:
   an aerosol container;
   a discharge piece mounted to the aerosol container;
   a flow control valve mounted within the discharge piece;
   a battery;
   an electronically controlled metering valve electronically connected to the battery and in fluid communication with the flow control valve, wherein the flow control valve is movable between an open position wherein a volume of an aerosol formulation is directed from the aerosol container through the flow control valve to the metering valve, and a closed position wherein the aerosol formulation is not permitted to flow through the flow control valve to the metering valve, and wherein the metering valve is configured to precisely control a flow of the aerosol formulation outward of the discharge piece; and
   a solenoid electronically connected to the battery, wherein the solenoid is movable between an actuated position wherein the solenoid urges the flow control valve into the open position, and an un-actuated position wherein the solenoid does not act on the flow control valve and the flow control valve remains in the closed position.

2. The aerosol dispensing apparatus according to claim 1, wherein the flow control valve is configured as an on-off valve.

3. The aerosol dispensing apparatus according to claim 2, wherein the electronically controlled metering valve is an electronically actuated microvalve.

4. The aerosol dispensing apparatus according to claim 3, further including a microcontroller electronically connected between the battery and the microvalve and configured to control a dose amount of the aerosol formulation dispensed through the microvalve.

5. The aerosol dispensing apparatus according to claim 4, wherein the dose amount of the aerosol formulation is measured by a volume of the aerosol formulation dispensed through the microvalve.

6. The aerosol dispensing apparatus according to claim 5, wherein the dose amount of the aerosol formulation is measured by a duration of a flow of an aerosol formulation dispensed through the microvalve.

7. The aerosol dispensing apparatus according to claim 3, further including a manually actuated switch between the battery and the microvalve and in an outside surface of the aerosol dispensing apparatus, the switch operative to move the microvalve between the open and closed positions.

* * * * *